(12) United States Patent
Andreasson et al.

(10) Patent No.: US 7,200,199 B2
(45) Date of Patent: Apr. 3, 2007

(54) X-RAY DIAGNOSTIC DEVICE FOR MAMMOGRAPHY EXAMINATIONS

(75) Inventors: Jesper Andreasson, Jaerfaella (SE); Stefan Karlsson, Sollentuna (SE)

(73) Assignee: Siemens Aktiengesellschaft, Munich (DE)

( * ) Notice: Subject to any disclaimer, the term of this patent is extended or adjusted under 35 U.S.C. 154(b) by 149 days.

(21) Appl. No.: 10/920,171

(22) Filed: Aug. 18, 2004

(65) Prior Publication Data
US 2005/0058241 A1    Mar. 17, 2005

(30) Foreign Application Priority Data
Aug. 18, 2003    (DE)    ................. 103 37 936

(51) Int. Cl.
*A61B 6/04* (2006.01)
(52) U.S. Cl. ........................... 378/37; 378/155
(58) Field of Classification Search ............... 378/37, 378/154, 155, 186
See application file for complete search history.

(56) References Cited

U.S. PATENT DOCUMENTS 4,542,521 A * 9/1985 Hahn et al. ................ 378/155
2005/0063509 A1 * 3/2005 Defreitas et al. ............ 378/37
2005/0111617 A1 * 5/2005 Shoji ........................ 378/37

* cited by examiner

*Primary Examiner*—Edward J. Glick
*Assistant Examiner*—Jurie Yun
(74) *Attorney, Agent, or Firm*—Harness, Dickey & Pierce, P.L.C.

(57) ABSTRACT

An X-ray diagnostic device is for mammography examinations and includes an arm for an X-ray tube and an object table having an image receptor. The X-ray tube is able to emit a radiation field towards the image receptor. Further, an X-ray grid is included, that is introducable into the radiation field, as well as an attachment unit that can be attached to the object table. In order to obtain an X-ray diagnostic unit having an arrangement that eliminates the risk of exposing the patient to be examined to an unnecessarily high dose of X-ray radiation, the object table is provided with a sensing arrangement that is connected to a transport device for the X-ray grid. Upon applying the attachment unit to the object table, the attachment unit actuates the sensing arrangement in such a way that the transport device transports the X-ray grid out of the radiation field.

7 Claims, 3 Drawing Sheets

X-RAY DIAGNOSTIC DEVICE FOR MAMMOGRAPHY EXAMINATIONS

The present application hereby claims priority under 35 U.S.C. §119 on German patent application number DE 103 37 936.3 filed Aug. 18, 2003, the entire contents of which are hereby incorporated herein by reference.

FIELD OF THE INVENTION

The invention generally relates to an X-ray diagnostic device for mammography examinations. Preferably, it relates to a device having an arm for an X-ray tube and having an object table having an image receptor. The X-ray tube is preferably able to emit a radiation field towards the image receptor. The device further preferably includes an X-ray grid, an attachment unit that can be attached to the object table, and a compression plate, arranged between the X-ray tube and the object table, which is connected to the arm and can be moved along the arm.

BACKGROUND OF THE INVENTION

A brochure from the Siemens company entitled "MAM-MOMAT 3000 Nova" shows an X-ray diagnostic unit for mammography examinations. The attachment unit mentioned in the introduction may be a biopsy unit, as shown in the brochure, for taking tissue samples from a breast, or else a magnification table as shown in the brochure from the KRAMEX company entitled "AVIVA The Mammography System Designed to Grow with Technology".

Used in conjunction with magnification i.e. when a magnification table is attached to an object table or to an image receptor, the table surface of the magnification attachment unit happens to lie at a distance from the image receptor. When taking an X-ray photograph of a breast, the X-ray grid mentioned in the introduction is normally used to reduce the stray X-ray radiation which causes a detectable deterioration in the image quality. When magnification is used, however, an X-ray grid is not used. This is because, with a magnification table attached, the stray radiation does not cause a degradation in the image quality when taking a photograph, owing to the space created between the table surface of the magnification table and the image receptor. An X-ray grid is also not used for a biopsy examination because in this case just a small section of the breast is irradiated.

If an operator forgets to move the X-ray grid out of the X-ray field when using magnification or when performing a biopsy examination, an unnecessarily high X-ray dose can accidentally be given to the breast to be examined in order to obtain a good image quality, because the X-ray grid absorbs a large proportion of the X-ray dose.

SUMMARY OF THE INVENTION

An object of an embodiment of the invention is to create an X-ray diagnostic unit having an arrangement that reduces the risk of exposing the patient to be examined to an unnecessarily high dose of X-ray radiation.

An object may be achieved according to an embodiment of the invention by providing the object table with a sensing arrangement that is connected to a transport device for the X-ray grid. When applying the attachment unit to the object table, the attachment unit preferably actuates the sensing arrangement in such a way that the transport device transports the X-ray grid out of the radiation field. The automatic transportation of the X-ray grid out of the X-ray field when the magnification table or the biopsy unit is applied to the object table ensures that the patient receives only the minimum X-ray dose that is necessary to obtain a good X-ray image quality.

BRIEF DESCRIPTION OF THE DRAWINGS

Further advantages, features and details of the invention will become evident from the description of illustrated exemplary embodiments given hereinbelow and the accompanying drawings, which are given by way of illustration only and thus are not limitative of the present invention, wherein.

DETAILED DESCRIPTION OF THE PREFERRED EMBODIMENTS OF THE INVENTION

Figure 1:
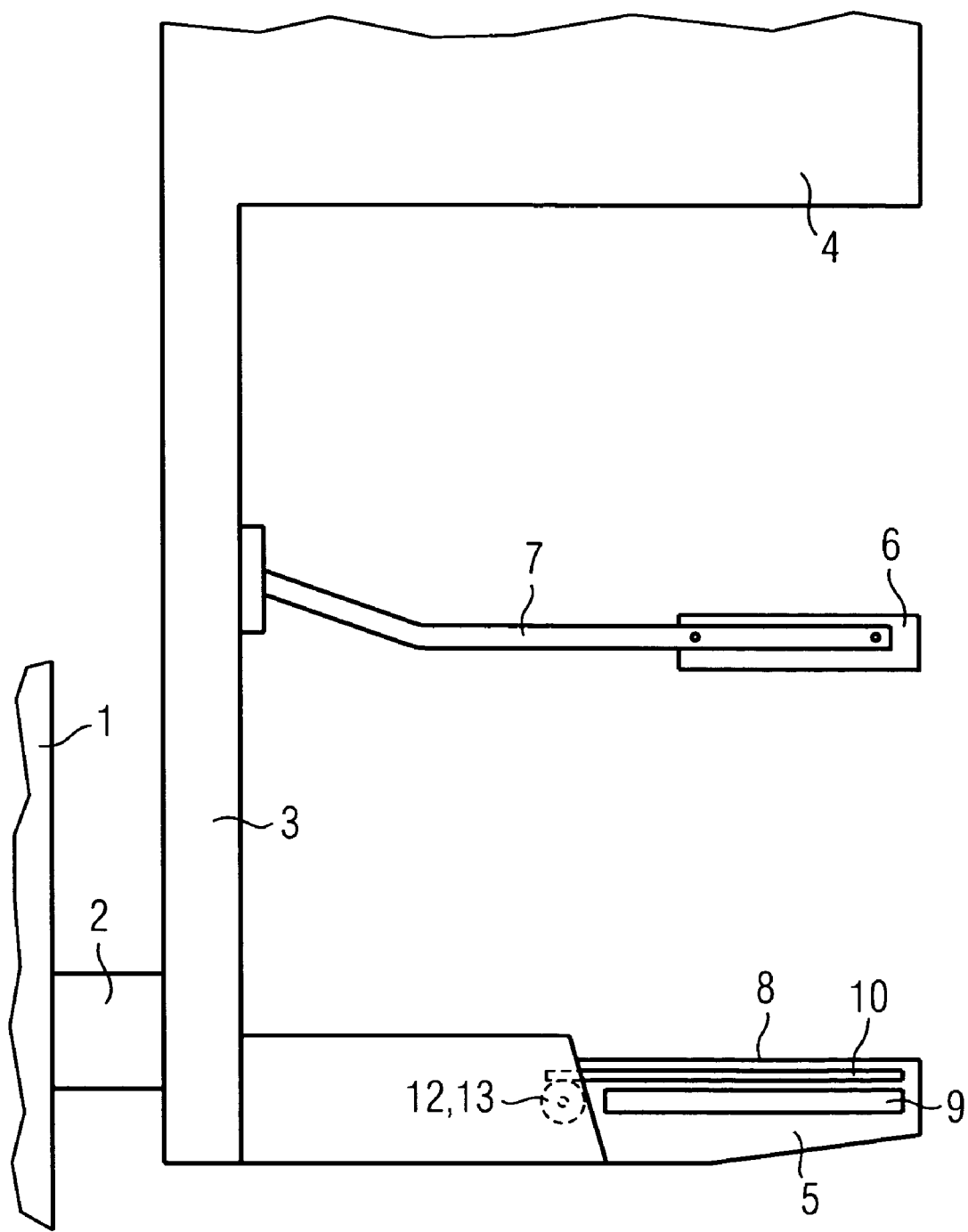
FIG. 1 shows a side view of a section of an X-ray diagnostic unit for mammography examinations according to an embodiment of the invention.

FIG. 1 shows a side view of a section of an X-ray diagnostic unit for mammography examinations. A device stand 1 is shown in FIG. 1 that is connected via a shaft 2 to an arm 3 for an X-ray tube and an object table 5. A compression plate 6 is arranged between the X-ray tube 4 and the object table 5 and is connected via a bracket 7 to the arm 3 along which it can move.

The object table 5 includes a table surface 8, an image receptor 9 and an X-ray grid 10 arranged between the table surface 8 and the image receptor 9. A transport device for the X-ray grid 10 is also located in the object table 5 and is shown in FIG. 2 and described in more detail with reference to this figure.

Figure 2:
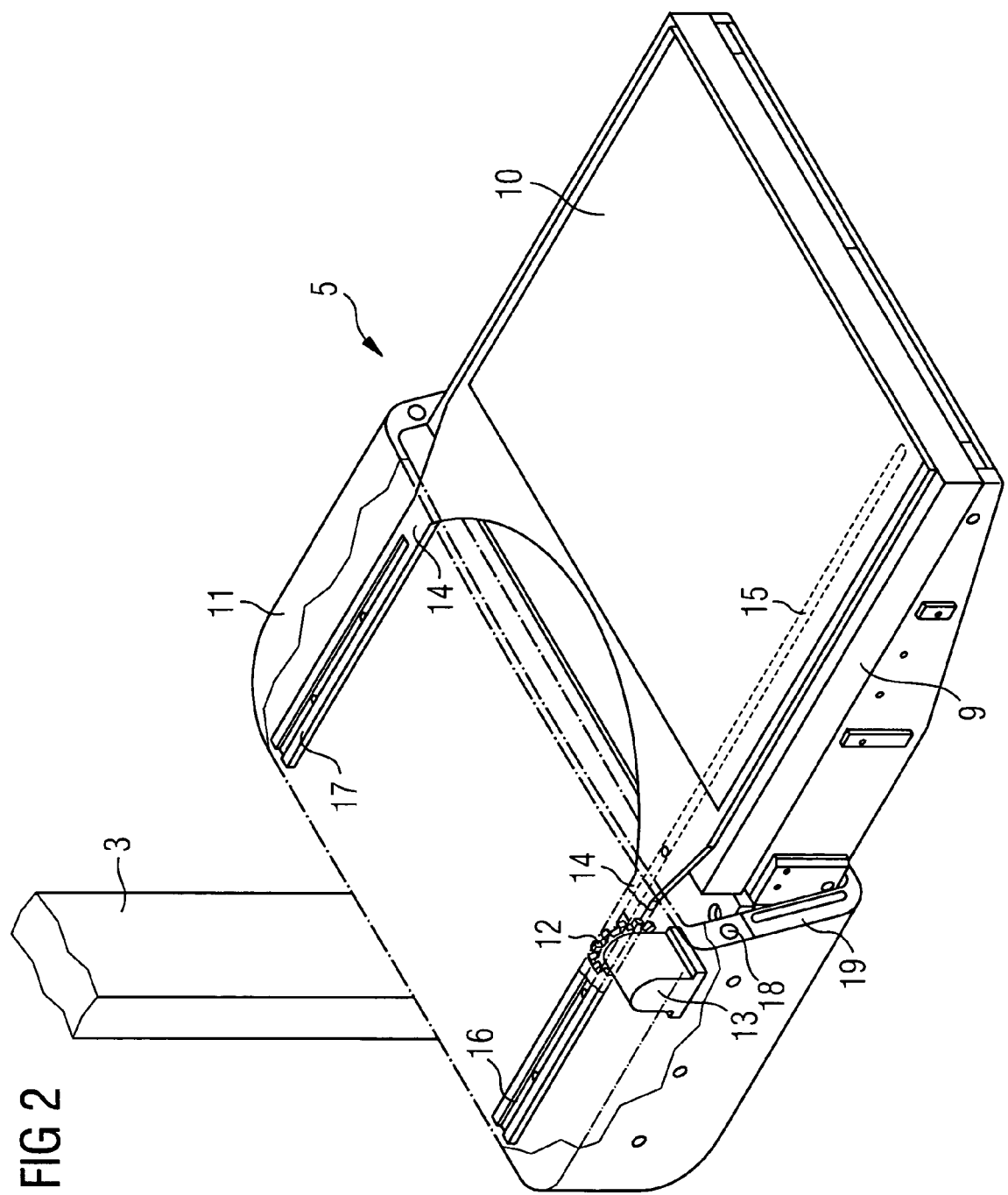
FIG. 2 shows a perspective view of an object table of the X-ray diagnostic unit shown in FIG. 1.

FIG. 2 shows a perspective view of the object table 5. The table surface 8 (FIG. 1) has been removed in the figure to provide a clear view of the X-ray grid 10. A housing 11 for the object table 5 has been indicated simply by dashed lines to provide a clearer view of the transport device mentioned in FIG. 1. The transport device is provided in order to transport the X-ray grid 10 from the position shown in FIG. 2 into another position in which the grid 10 is displaced into the housing 11, so that the image receptor 9 is exposed. The transport device is provided with a toothed wheel 12 that is connected to a motor 13 arranged in the housing 11. The X-ray grid 10 has an extension piece 14 that extends into the housing 11.

The X-ray grid 10 is provided with a toothed rack 15 that extends over the one longitudinal side of the grid 10 and along its extension piece 14. The toothed rack 15, which is attached to the grid 10, is arranged between the grid 10 and the image receptor 9. The teeth of the toothed rack 15 are always engaged with the toothed wheel 12 irrespective of the position of the grid 10.

Rails 16, 17 are located in the housing 11 of the object table 5 and are intended to ensure a stable and secure displacement of the grid 10 when transporting the grid 10. The extension piece 14 is connected to the rails 16, 17 by devices/methodology known in the art and hence not described. The object table 5 is also provided with a sensing arrangement 18, e.g. in the form of a sensor, that is electrically connected to the motor 13. The sensor 18 can preferably be attached to the end face 19 of the housing 11.

Figure 3:
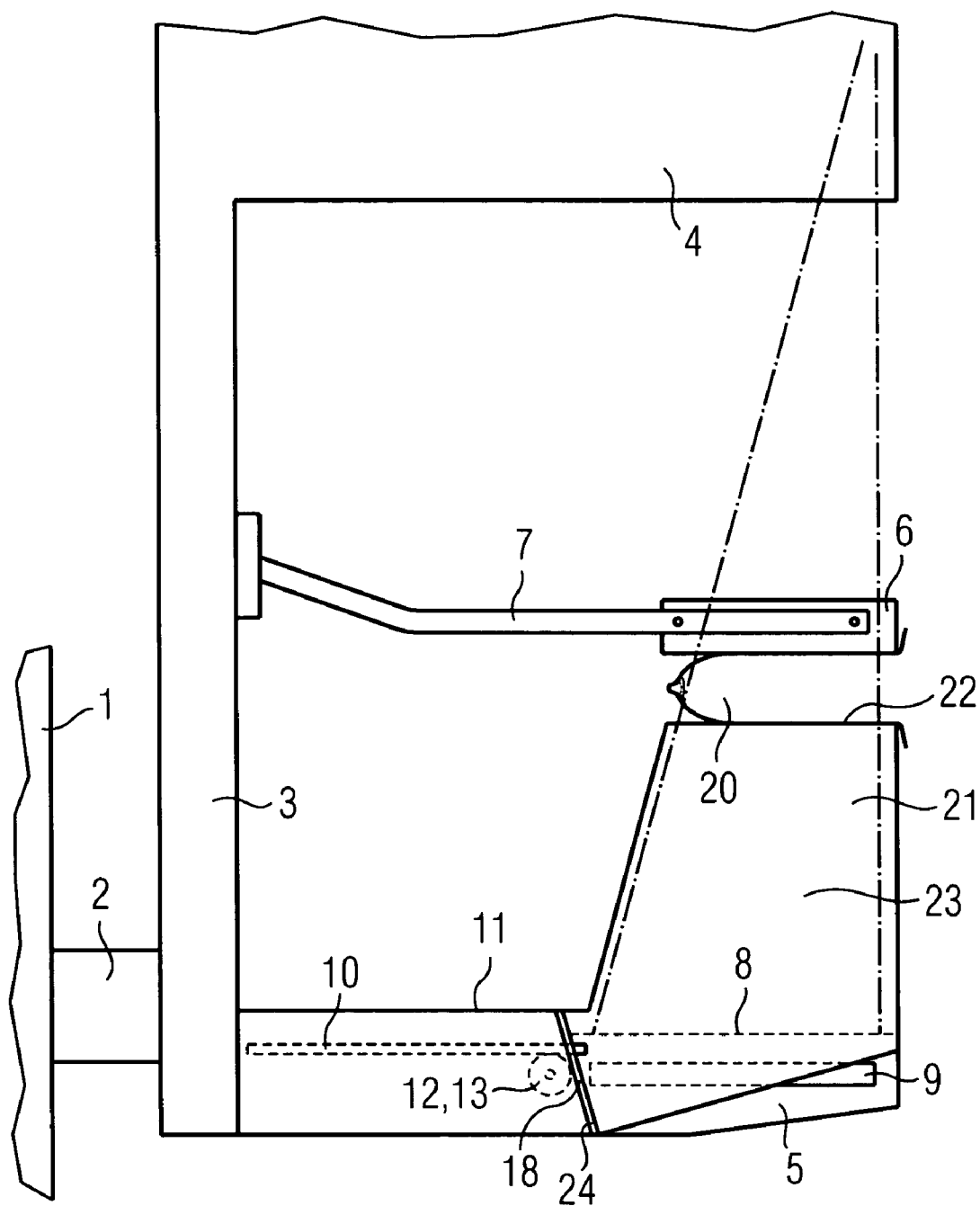
FIG. 3 shows a further side view of the X-ray diagnostic unit shown in FIGS. 1 and 2.

FIG. 3 shows a magnification table 21 that is attached to the object table. The figure also shows the breast 20 to be examined which is placed on the table surface 22 of the magnification table 21 prior to taking a photograph, and is compressed using the compression plate 6.

Since, as already explained in detail, it is not desirable when using magnification for the X-ray grid 10 to be located in the X-ray field 23 generated by the X-ray tube 4, the X-ray grid 10 is guided automatically out of the X-ray field when the magnification table 21 is applied to the object table 5. This is achieved by the end face 24 of the magnification table 21, which lies against the end face 19 of the housing 11 after the said application, pressing against the sensor 18. The sensor 18 now actuates the motor 13 such that the toothed wheel 12 is turned in such a direction that the toothed rack 15 connected to the toothed wheel 12, and hence also the X-ray grid 10, is transported into the housing 11.

When, after magnification, the magnification table 21 is removed from the object table, the sensor 18 is de-actuated, whereby the toothed wheel 12 is turned using the motor 13 in such a direction that the toothed rod 15, and hence also the X-ray grid 10, is transported back into its original position.

The X-ray grid 10 is transported in the same way when, instead of the magnification table, a biopsy unit (not shown here) is applied to the object table 5.

For the transport process, the X-ray diagnostic unit comprises, in a way not shown, limit switches known in the art so that the motor 13 is switched off automatically, i.e. the process of transporting the X-ray grid 10 is terminated, when the X-ray grid 10 has reached its parked position in the housing 11 or its position above the image receptor 9.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. X-ray diagnostic unit for mammography examinations, comprising:
    an arm for supporting an X-ray tube and a bracket, the bracket supporting a compression plate;
    an object table including an image receptor, said X-ray tube being able to emit a radiation field towards the image receptor; an X-ray grid, introducible into the radiation field; and
    an attachment unit, attachable to the object table, wherein the object table includes a sensing arrangement connected to a transport device for the X-ray grid, whereby upon applying the attachment unit to the object table, the attachment unit actuates the sensing arrangement in such a way that the transport device transports the X-ray grid out of the radiation field and into a housing separate from the arm.

2. An X-ray diagnostic unit, comprising:
    an object table including an image receptor, wherein the image receptor is adapted to receive an emitted radiation field;
    an X-ray grid, introducible into the radiation field; and
    an attachment unit, attachable to the object table, wherein the object table includes a sensing arrangement operatively connected to a transport device for the X-ray grid, whereby upon applying the attachment unit to the object table, the attachment unit is adapted to actuate the sensing arrangement in such a way that the transport device is adapted to transport the X-ray grid out of the radiation field and into a housing independent from an arm for supporting an x-ray tube and a bracket, the bracket supporting a compression plate.

3. The X-ray diagnostic unit of claim 2, wherein the X-ray diagnostic unit is for mammography examinations.

4. An X-ray diagnostic unit, comprising:
    an object table including means for receiving an emitted radiation field;
    a grid, introducible into the radiation field; and
    means, upon attaching to the object table, for actuating a sensor arrangement of the object table, the actuated sensor arrangement triggering transporting of the grid out of the radiation field and into a housing, the housing being separate from an arm for supporting an x-ray tube and a bracket, the bracket supporting a compression plate.

5. The X-ray diagnostic unit of claim 4, wherein the X-ray diagnostic unit is for mammography examinations.

6. The X-ray diagnostic unit of claim 4, wherein the actuated sensor arrangement triggers a transport device, transporting the grid.

7. In X-ray diagnostic unit including an object table including an image receptor adapted to receive an emitted radiation field, an X-ray grid, and an attachment unit, attachable to the object table, a method comprising:
    applying the attachment unit to the object table;
    sensing the applying of the attachment unit; and
    transporting the X-ray grid out of the radiation field and into a housing separate from an arm for supporting an x-ray tube and a bracket, the bracket supporting a compression plate, in response to the sensing.

* * * * *